United States Patent [19]

Zimmerman et al.

[11] Patent Number: 4,649,132

[45] Date of Patent: Mar. 10, 1987

[54] TREATMENT OF FACTOR VIII INHIBITORS

[75] Inventors: Theodore S. Zimmerman; Carol A. Fulcher, both of La Jolla, Calif.

[73] Assignee: Scripps Clinic and Research Foundation, La Jolla, Calif.

[21] Appl. No.: 738,134

[22] Filed: May 24, 1985

Related U.S. Application Data

[63] Continuation-in-part of Ser. No. 481,105, Mar. 31, 1983, Ser. No. 556,508, Nov. 30, 1983, and Ser. No. 673,916, Nov. 21, 1984.

[51] Int. Cl.[4] .......................... A61K 37/43; C07K 7/10
[52] U.S. Cl. ......................................... 514/12; 530/324
[58] Field of Search ...................... 260/112 B; 514/12; 530/324

[56] References Cited

U.S. PATENT DOCUMENTS 4,361,509  11/1982  Zimmerman et al. .......... 260/112 B

OTHER PUBLICATIONS

Biol. Abstr., vol. 79, p. 37707.
Biol. Abstr., vol. 79, p. 83116.
Blood, vol. 59, No. 3 (1982) 594–600.
The Journal of Biological Chem., 252, (1977) 3587–3598.
Biochem., 19, No. 3, (1980) 401–410.
Blood, 59, (1982) 615–624.
201, USPQ, 70–77.
Proc. Nat'l. Acad. Sci., 79, 1648–1652, (1982).
Biochemistry (1980) 19, 4859–4864.
The Journal of Biochemistry, 254 (1979) 1326–1334.
The Journal of Biol. Chemistry, 257, 6556–6564 (1982).
J. Lab. Clin. Med. (1981) 97, 50–64.
Immunochemistry (1971) vol. 8, pp. 871–874.
Anal. Biochem. 56, 361–369 (1973).
Biochemistry, 10, (1971) 2606–2617.
Nature, vol. 227, (1970) 680–685.
Proc. Nat'l. Acad. Sci., 79, 7200–7204.

*Primary Examiner*—Delbert R. Phillips
*Attorney, Agent, or Firm*—Morgan & Finnegan

[57] ABSTRACT

Fragments of human Factor VIII:C which bind to antibody inhibitors of Factor VIII in patients afflicted with such inhibitors are disclosed. The method of treating Factor VIII inhibitors, by administering one or more of these fragments, is also disclosed.

33 Claims, No Drawings

TREATMENT OF FACTOR VIII INHIBITORS

This application is a continuation-in-part of our pending applications Ser. No. 481,105, filed Mar. 31, 1983; Ser. No. 556,508, filed Nov. 30, 1983; and Ser. No. 673,916, filed Nov. 21, 1984.

This invention relates to the treatment of patients who exhibit Factor VIII inhibitors.

The conventional treatment for hemophilia-A is administration of Factor VIII (antihemophilic factor, or "AHF"), concentrated in any of various means from the plasma of donors. Some hemophiliacs exhibit, in effect, "resistance" to this treatment, in that administration of Factor VIII in doses which are usually effective for most hemophiliacs produces reduced or no therapeutic effect. In addition, persons who are not hemophiliacs can develop these inhibitors.

This phenomenon has generally been considered to be due to one or more anti-Factor VIII antibody inhibitors of Factor VIII in the circulatory system of the afflicted individual. It may be possible to treat Factor VIII inhibitors by administering greatly increased amounts of Factor VIII, some of which serves to saturate the inhibitory capacity of the Factor VIII inhibitor and the remainder of which provides the desired therapeutic effect uninhibited. However, this approach is extremely expensive, consumes large amounts of AHF per patient, and carries the risk of increasing the amounts of other products or agents, unavoidably present with the Factor VIII, to which the patient is exposed.

Thus, there is a need for a product which effectively neutralizes the activity of Factor VIII inhibitors, without introducing unnecessary co-products.

SUMMARY OF THE INVENTION

The present invention comprises a polypeptide having the amino acid sequence of the fragment of human Factor VIII containing amino acid residues 1690-2332. It also comprises a polypeptide having the amino acid sequence of the fragment of human Factor VIII containing amino acid residues 373-740. In addition, it comprises fragments of human Factor VIII containing either of these polypeptides. These polypeptides have been found to react immunologically with Factor VIII inhibitors.

The invention further comprises a polypeptide which neutralizes the activity of Factor VIII inhibitor and whose amino acid sequence is that of a fragment of human Factor VIII selected from the group consisting of (i) fragments whose amino-terminal residue is one of residues 360-380 and whose carboxyl-terminal residue is one of residues 394-465;

(ii) fragments whose amino-terminal residue is one of residues 395-466 and whose carboxyl-terminal residue is one of residues 472-492;

(iii) fragments whose amino-terminal residue is one of residues 360-380 and whose carboxyl-terminal residue is one of residues 472-492;

(iv) fragments whose amino-terminal residue is one of residues 1674-1694 and whose carboxyl-terminal residue is one of residues 1708-1775;

(v) fragments whose amino-terminal residue is one of residues 1709-1776 and whose carboxyl-terminal residue is one of residues 1782-1802; and (vi) fragments whose amino-terminal residue is one of residues 1674-1694 and whose carboxyl-terminal residue is one of residues 1782-1802.

Particularly preferred are polypeptides whose amino acid sequences are those of fragments of human Factor VIII having any of the following sequences:

(i) amino acid residues 380-394;
(ii) amino acid residues 466-472;
(iii) amino acid residues 380-472;
(iv) amino acid residues 1694-1708;
(v) amino acid residues 1776-1782; or
(vi) amino acid residues 1694-1782.

The invention further comprises the method of suppressing or neutralizing Factor VIII inhibitors in a patient who exhibits such inhibitors, by administering to the patient an effective amount of one or more of these polypeptides.

DETAILED DESCRIPTION OF THE INVENTION

When amino acid residues of human Factor VIII are referred to herein by number, the numbering of the amino acid residues is that reported by Vehar, G. A., et al., "Structure of human factor VIII" in Nature, Vol. 312: 337-342 (1984).

For instance, the polypeptide whose amino acid sequence is that of the fragment having residues 380-394 is:

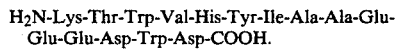

The polypeptide whose sequence is residues 466-472 is:

The polypeptide whose sequence is residues 1694-1708 is:

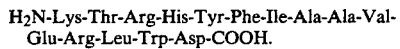

The polypeptide whose sequence is residues 1776-1782 is:

The present invention encompasses these polypeptides of interest, as well as polypeptides which contain the amino acid sequences of these polypeptides of interest plus flanking residues at one or both ends thereof. When we refer to the "flanking residues" at an end of a given fragment, we mean the residue(s) immediately adjacent to that end of the fragment, in the sequence in which they appear in the published sequence reported for the Factor VIII polypeptide. For instance, the single flanking residues of the polypeptide whose sequence is that of the fragment of Factor VIII containing residues 466-472 are residues 465 at the amino-terminal end, and 473 at the carboxyl-terminal end. The five flanking residues are residues 461-465 at the amino-terminal end, and residues 473-477 at the carboxyl-terminal end. In addition to the polypeptides of interest described above, polypeptides incorporating any of those sequences and, at either end or at each end, up to 20 flanking residues, or up to 10, or even 1-5 flanking residues, are also of interest in this invention.

The fragment of Factor VIII containing amino acid residues 1690–2332 is the fragment of $M_r$ about 72,000 described in our earlier patent applications Ser. No. 481,105, Ser. No. 556,508, and Ser. No. 673,916, the contents of which are hereby incorporated by reference. This fragment is formed by thrombin-induced proteolysis of the fragment of $M_r$ about 80,000 described therein. The fragment containing amino acid residues 373–740 is the fragment of $M_r$ about 44,000 described in those earlier applications.

The fragments of the present invention can be formed by solid-state synthesis or by recombinant DNA techniques.

In the well-known procedure for solid state synthesis of a polypeptide, the desired polypeptide is assembled starting from an insoluble support such as benzhydryl amine or chloromethylated resin (derived from cross-linked polystyrene, and available from chemical supply houses). The amino acid at the carboxyl terminal end of the desired polypeptide, carrying protecting groups on the alpha-amino nitrogen and on any other reactive sites, is attached to the the resin from solution using known peptide coupling techniques. The protecting group on the alpha-amino group is removed (leaving other protecting groups, if any, intact), and the next amino acid of the desired sequence (carrying suitable protecting groups) is attached, and so on. When the desired polypeptide has been completely built up, it is cleaved from the resin support, all protecting groups are removed, and the polypeptide is recovered. Examples of suitable protecting groups are: alpha-tert-butyloxycarbonyl for the alpha-amino-group; benzyl, 4-methoxybenzyl, or 4-methylbenzyl for the thiol group of cysteine, the beta-carboxylic acid group of aspartic acid, the gamma-carboxylic acid group of glutamic acid, and the hydroxyl groups of serine, threonine, and tyrosine; benzyloxycarbonyl or a 2-chloro- or 3,4-dimethoxy-derivative thereof for the ring nitrogens of histidine and tryptophan and the epsilon-amino group of lysine; p-nitrophenyl for the amide nitrogens of asparagine and glutamine; and nitro or tosyl for the guanidine group of arginine.

To make the desired polypeptide by recombinant DNA techniques, the portion of the gene for human Factor VIII that codes for the fragment of interest is cloned, inserted into a cell, and used to express the fragment. For a description of the gene and how to use it, see Gitschier, J., et al., "Characterization of the human factor VIII gene", Nature, Vol. 312, pp. 326–330; Wood, William I., et al., "Expression of active human factor VIII from recombinant DNA clones", Nature, Vol. 312, pp. 330–337; and Toole, John J., et al., "Molecular cloning of a cDNA encoding human antihemophilic factor", Nature, Vol. 312, pp. 342–347.

The manner of making the fragments having $M_r$ values of about 80,000, about 72,000 and about 44,000, as described in our earlier applications is summarized as follows. Factor VIII is purified and concentrated, preferably to a high degree such as by the process described in our U.S. Pat. No. 4,361,509. In that process, Factor VIII (termed Factor VIII:C in that patent) and Factor VIII:RP are adsorbed together from a source such as commercial AHF concentrate onto a monoclonal antibody to Factor VIII:RP which is bound to a solid substrate such as cross-linked agarose (e.g. Sepharose). The other source materials are eluted, and then the Factor VIII is eluted and passed through a second column such as aminohexyl agarose to further purify and concentrate the Factor VIII.

The resulting highly purified Factor VIII is then digested with alpha-thrombin under conditions effective to react with the Factor VIII to form the desired fragments, without completely digesting the Factor VIII. For instance, 200 to 400 units/ml of Factor VIII and 0.1 to 0.5 units/ml of alpha-thrombin can be combined at room temperature in an aqueous system, buffered to a pH of about 6.8 to 7.4. After the reaction has been allowed to proceed long enough for the desired fragment (or fragments) to have formed, the digestion is discontinued by addition of a product which irreversibly inhibits the alpha-thrombin without degrading the Factor VIII fragments. A highly satisfactory product is (p-amidino-phenyl)methanesulfonyl fluoride ("p-APMSF"), in an amount on the order of 1.0 micromoles to 2.5 millimoles per unit of alpha-thrombin initially present. The appropriate period of reaction time before addition of the thrombin inhibitor depends somewhat on which fragment is desired. In general, the fragments having $M_r$ values of about 80,000 and about 72,000 are present as little as 0.1 minute after addition of the alpha-thrombin to the Factor VIII, and remain present for as long as 60 minutes or more of reaction time. The fragment of $M_r$ about 44,000 may form as quickly, but is likely to be present in a greater proportion after about 2 minutes of digestion, through about 60 minutes or longer.

Following inactivation of the alpha-thrombin, the resulting mixture of Factor VIII fragments is treated to recover the desired fragment(s) by conventional techniques for concentration and recovery of polypeptides. Useful techniques include ultrafiltration, ultracentrifugation, ion exchange, gel permeation chromatography, preparative electrophoresis, isoelectric focusing, and gel and affinity chromatography (including affinity chromatography using an antibody to the desired fragment). In particular, sodium dodecyl sulfate-polyacrylamide gel electrophoresis, preferably the Procedure A described in our application Ser. No. 481,105 and incorporated herein by reference, can be used to separate the mixture of fragments into discrete bands (each of which contains a different fragment). One or more of the above techniques are used to recover each fragment, preferably free of other non-Factor VIII products and preferably free of Factor VIII and other Factor VIII fragments.

Each fragment can be recovered as an aqueous solution which may be treated to remove water therefrom by procedures well known in the art. For instance, the mixture can be freeze-dried, or ultrafiltered and then freeze-dried.

The dried compositions containing one or more of the polypeptides of the present invention can be formulated into pharmaceutical preparations for therapeutic, diagnostic, or other uses. To prepare them for intravenous administration, the compositions are dissolved in water containing physiologically compatible substances such as sodium chloride (e.g. 0.35–2.0 M), glycine, and the like and having a buffered pH compatible with physiological conditions. The amount to administer will depend on the severity with which the patient is afflicted with Factor VIII inhibitors, but can be determined readily for any particular patient. Sufficient neutralizer of the inhibitor should be given to reduce or eliminate the inhibition of the effect of a subsequently administered preparation containing Factor VIII.

The Factor VIII fragments of amino acid residues 1690-2332, and of amino acid residues 373-740, have been found to bind inhibitors of Factor VIII inhibitor in plasma obtained from patients known to exhibit Factor VIII inhibitory activity. This indicates that a Factor VIII fragment which contains either of those fragments would also neutralize Factor VIII inhibitor activity, and could be administered to suppress a patient's production of Factor VIII inhibitors. The present invention also encompasses fragments within those longer fragments which neutralize Factor VIII inhibitor activity. Factor VIII inhibitor neutralizing polypeptides having the amino acid sequence of any of these fragments are also useful in diagnosing the presence of Factor VIII inhibitors.

In general, the polypeptide is contacted with a sample of the plasma or blood being tested, and the mixture is then analyzed to determine whether the polypeptide has reacted with an antibody inhibitor. Such a process can employ, for instance, the technique known as "Western blotting". For example, a Factor VIII inhibitor neutralizing polypeptide is transferred by known techniques to a nitrocellulose sheet, where it is immobilized. By "immobilized" we mean fixed or bonded to a solid support so that the protein can be contacted with successive liquid reagent samples without being washed out of the substrate. A sheet such as nitrocellulose is of course preferred as it facilitates the autoradiography step.

The immobilized polypeptide is then washed with the sample being tested. To test whether any protein in the sample has reacted (immunologically) with the immobilized polypeptide, (and thereby become bound to it) the latter is contacted (e.g. washed) with monoclonal antibodies to human IgG (such as 0.25 µg/ml of one or more of mouse monoclonal antibodies to human IgG-1, IgG-2, IgG-3 or IgG-4 as for instance 0.01% processed ascites fluid (Miles Scientific, Naperville, Ill.)). Then, the immobilized polypeptide is visualized by reacting it with e.g. $^{125}$I-labeled rabbit anti-mouse IgG (or another labeled purified antibody to the anti-human IgG used in the previous step) and then subjecting it to autoradiography in known fashion. The presence of a band indicates the presence of Factor VIII inhibitor in the tested plasma.

What is claimed is:

1. A polypeptide which neutralizes the activity of Factor VIII inhibitor and whose amino acid sequence is that of a fragment of human Factor VIII selected from the group consisting of:
   (i) fragments whose amino-terminal residue is one of residues 360-380 and whose carboxyl-terminal residue is one of residues 394-465;
   (ii) fragments whose amino-terminal residue is one of residues 395-466 and whose carboxyl-terminal residue is one of residues 472-492;
   (iii) fragments whose amino-terminal residue is one of residues 360-380 and whose carboxyl-terminal residue is one of residues 472-492;
   (iv) fragments whose amino-terminal residue is one of residues 1674-1694 and whose carboxyl-terminal residue is one of residues 1708-1775;
   (v) fragments whose amino-terminal residue is one of residues 1709-1776 and whose carboxyl-terminal residue is one of residues 1782-1802; and
   (vi) fragments whose amino-terminal residue is one of residues 1674-1694 and whose carboxyl-terminal residue is one of residues 1782-1802.

2. A polypeptide which neutralizes the activity of Factor VIII inhibitor and whose amino acid sequence is that of a fragment of human Factor VIII selected from the group consisting of
   (i) amino acid residues 380-394;
   (ii) amino acid residues 466-472;
   (iii) amino acid residues 380-472;
   (iv) amino acid residues 1694-1708;
   (v) amino acid residues 1776-1782; and
   (vi) amino acid residues 1694-1782.

3. A polypeptide according to claim 2 whose amino acid sequence is that of the fragment of human Factor VIII composed of amino acid residues 380-394.

4. A polypeptide according to claim 2 whose amino acid sequence is that of the fragment of human Factor VIII composed of amino acid residues 466-472.

5. A polypeptide according to claim 2 whose amino acid sequence is that of the fragment of human Factor VIII composed of amino acid residues 380-472.

6. A polypeptide according to claim 2 whose amino acid sequence is that of the fragment of human Factor VIII composed of amino acid residues 1694-1708.

7. A polypeptide according to claim 2 whose amino acid sequence is that of the fragment of human Factor VIII composed of amino acid residues 1776-1782.

8. A polypeptide according to claim 2 whose amino acid sequence is that of the fragment of human Factor VIII composed of amino acid residues 1694-1782.

9. A Factor VIII inhibitor neutralizing polypeptide whose amino acid sequence is that of the fragment of human Factor VIII composed of amino acid residues 1690-2332, and which is essentially free of other fragments of human Factor VIII.

10. A Factor VIII inhibitor neutralizing polypeptide whose amino acid sequence is that of the fragment of human Factor VIII composed of amino acid residues 373-740, and which is essentially free of other fragments of human Factor VIII.

11. A Factor VIII inhibitor neutralizing product comprising polypeptides whose amino acid sequences are those of the fragments of human Factor VIII composed of amino acid residues 1690-2332 and 373-740, and which is essentially free of other fragments of human Factor VIII.

12. A therapeutic composition comprising an amount of one or more polypeptides according to claim 1 effective to neutralize Factor VIII inhibitor activity in a patient exhibiting such activity, in association with a pharmaceutically acceptable carrier.

13. A therapeutic composition comprising an amount of one or more polypeptides according to claim 2 effective to neutralize Factor VIII inhibitor activity in a patient exhibiting such activity, in association with a pharmaceutically acceptable carrier.

14. A therapeutic composition comprising an amount of a polypeptide according to claim 3 effective to neutralize Factor VIII inhibitor activity in a patient exhibiting such activity, in association with a pharmaceutically acceptable carrier.

15. A therapeutic composition comprising an amount of a polypeptide according to of claim 4 effective to neutralize Factor VIII inhibitor activity in a patient exhibiting such activity, in association with a pharmaceutically acceptable carrier.

16. A therapeutic composition comprising an amount of a polypeptide according to claim 5 effective to neutralize Factor VIII inhibitor activity in a patient exhibiting such activity, in association with a pharmaceutically acceptable carrier.

17. A therapeutic composition comprising an amount of a polypeptide according to claim 6 effective to neutralize Factor VIII inhibitor activity in a patient exhibiting such activity, in association with a pharmaceutically acceptable carrier.

18. A therapeutic composition comprising an amount of a polypeptide according to claim 7 effective to neutralize Factor VIII inhibitor activity in a patient exhibiting such activity, in association with a pharmaceutically acceptable carrier.

19. A therapeutic composition comprising an amount of a polypeptide according to claim 8 effective to neutralize Factor VIII inhibitor activity in a patient exhibiting such activity, in association with a pharmaceutically acceptable carrier.

20. A therapeutic composition comprising an amount of a polypeptide according to claim 9 effective to neutralize Factor VIII inhibitor activity in a patient exhibiting such activity, in association with a pharmaceutically acceptable carrier.

21. A therapeutic composition comprising an amount of a polypeptide according to claim 10 effective to neutralize Factor VIII inhibitor activity in a patient exhibiting such activity, in association with a pharmaceutically acceptable carrier.

22. A therapeutic composition comprising an amount of a product according to claim 11 effective to neutralize Factor VIII inhibitor activity in a patient exhibiting such activity, in association with a pharmaceutically acceptable carrier.

23. A method of alleviating Factor VIII inhibitory activity in a patient suffering therefrom, comprising administering to such patient an effective amount of one or more polypeptides according to claim 1.

24. A method of alleviating Factor VIII inhibitory activity in a patient suffering therefrom, comprising administering to such patient an effective amount one or more polypeptides according to claim 2.

25. A method of alleviating Factor VIII inhibitory activity in a patient suffering therefrom, comprising administering to such patient an effective amount of a polypeptide according to claim 3.

26. A method of alleviating Factor VIII inhibitory activity in a patient suffering therefrom, comprising administering to such patient an effective amount of a polypeptide according to claim 4.

27. A method of alleviating Factor VIII inhibitory activity in a patient suffering therefrom, comprising administering to such patient an effective amount of a polypeptide according to claim 5.

28. A method of alleviating Factor VIII inhibitory activity in a patient suffering therefrom, comprising administering to such patient an effective amount of a polypeptide according to claim 6.

29. A method of alleviating Factor VIII inhibitory activity in a patient suffering therefrom, comprising administering to such patient an effective amount of a polypeptide according to claim 7.

30. A method of alleviating Factor VIII inhibitory activity in a patient suffering therefrom, comprising administering to such patient an effective amount of a polypeptide according to claim 8.

31. A method of alleviating Factor VIII inhibitory activity in a patient suffering therefrom, comprising administering to such patient an effective amount of a polypeptide according to claim 9.

32. A method of alleviating Factor VIII inhibitory activity in a patient suffering therefrom, comprising administering to such patient an effective amount of a polypeptide according to claim 10.

33. A method of alleviating Factor VIII inhibitory activity in a patient suffering therefrom, comprising administering to such patient an effective amount of a product according to claim 11.

* * * * *

UNITED STATES PATENT AND TRADEMARK OFFICE
CERTIFICATE OF CORRECTION

PATENT NO.   : 4,649,132
DATED        : March 10, 1987
INVENTOR(S)  : Zimmerman et al.

It is certified that error appears in the above-identified patent and that said Letters Patent is hereby corrected as shown below:

Line 1,

Column 1, after the title insert --This invention was made with government support under Grant Number HL 15491 awarded by The National Institute of Health. The government has certain rights to this invention.--

Signed and Sealed this

Twenty-eighth Day of June, 1994

Attest:

BRUCE LEHMAN

Attesting Officer        Commissioner of Patents and Trademarks